US011382923B2

(12) United States Patent
Shaik et al.

(10) Patent No.: US 11,382,923 B2
(45) Date of Patent: Jul. 12, 2022

(54) STABLE LIQUID FORMULATIONS OF CYCLOPHOSPHAMIDE AND PROCESSES TO PREPARE THE SAME

(71) Applicant: DR. REDDY'S LABORATORIES LIMITED, Hyderabad (IN)

(72) Inventors: Riyaz Ahmed Shaik, Hyderabad (IN); Ananya Saha, Asansol (IN); Svb Janardhan Garikipati, Visakhapatnam (IN); Akash Chaurasiya, Agra (IN); Bhavesh Vallabhbhai Patel, Hyderabad (IN); Harshal Bhagwatwar, Hyderabad (IN); Sumitra Ashok Pillai, Ahmedabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 141 days.

(21) Appl. No.: 15/402,712

(22) Filed: Jan. 10, 2017

(65) Prior Publication Data
US 2017/0143744 A1    May 25, 2017

Related U.S. Application Data

(63) Continuation-in-part of application No. PCT/IB2015/055285, filed on Jul. 13, 2015.

(30) Foreign Application Priority Data

Jul. 11, 2014   (IN) .......................... 3454/CHE/2014
Oct. 17, 2014   (IN) .......................... 5215/CHE/2014

(51) Int. Cl.
| | |
|---|---|
| *A61K 31/664* | (2006.01) |
| *A61K 9/08* | (2006.01) |
| *A61K 31/675* | (2006.01) |
| *A61K 9/19* | (2006.01) |
| *A61K 9/00* | (2006.01) |
| *A61K 47/10* | (2017.01) |
| *A61K 47/26* | (2006.01) |
| *A61K 47/44* | (2017.01) |
| *B01D 15/08* | (2006.01) |

(52) U.S. Cl.
CPC .......... *A61K 31/664* (2013.01); *A61K 9/0019* (2013.01); *A61K 9/08* (2013.01); *A61K 9/19* (2013.01); *A61K 31/675* (2013.01); *A61K 47/10* (2013.01); *A61K 47/26* (2013.01); *A61K 47/44* (2013.01); *B01D 15/08* (2013.01)

(58) Field of Classification Search
CPC .................................................. A61K 31/664
See application file for complete search history.

(56) References Cited

U.S. PATENT DOCUMENTS

| | | | |
|---|---|---|---|
| 3,018,302 A | 1/1962 | Arnold et al. | |
| 4,407,662 A * | 10/1983 | Ginder ................. | B01D 53/261 |
| | | | 203/19 |
| 4,537,883 A | 8/1985 | Alexander et al. | |
| 4,775,533 A | 10/1988 | Grab | |
| 4,879,286 A | 11/1989 | Alam et al. | |
| 4,952,575 A | 8/1990 | Sauerbier et al. | |
| 5,036,060 A | 7/1991 | Alam et al. | |
| 5,504,102 A | 4/1996 | Agharkar et al. | |
| 8,399,434 B2 | 3/2013 | Spasojevic et al. | |
| 2005/0272698 A1 | 12/2005 | Daftary et al. | |
| 2007/0265213 A1 | 11/2007 | Chakroun | |
| 2014/0005148 A1 | 1/2014 | Neelakantan et al. | |
| 2015/0320774 A1 * | 11/2015 | Palepu ................... | A61K 47/10 |
| | | | 514/110 |

FOREIGN PATENT DOCUMENTS

| | | |
|---|---|---|
| EP | 1023075 B1 | 12/2006 |
| WO | 2014/068585 A1 | 5/2014 |

OTHER PUBLICATIONS

Claims of U.S. Appl. No. 61/991,247 ("the '247 application") filed May 9, 2014.*
Specification of U.S. Appl. No. 61/991,247 ("the '247 application") filed May 9, 2014.*
Specification of U.S. Appl. No. 61/991,247, filed May 9, 2014.*
International Search Report dated Dec. 23, 2015, for corresponding International Patent Application No. PCT/IB2015/055285.
Written Opinion dated Dec. 23, 2015, for corresponding International Patent Application No. PCT/IB2015/055285.
International Preliminary Report on Patentability dated Jan. 17, 2017, for corresponding International Patent Application No. PCT/IB2015/055285.

* cited by examiner

*Primary Examiner* — Kevin E Weddington
(74) *Attorney, Agent, or Firm* — Pergament & Cepeda LLP; Milagros A. Cepeda; Edward D. Pergament

(57) ABSTRACT

The present invention relates to stable liquid pharmaceutical formulations of cyclophosphamide comprising cyclophosphamide and at least one pharmaceutically acceptable excipient wherein moisture content of the liquid formulation is less than about 2.0% by weight. The invention further relates to stable liquid formulations of cyclophosphamide prepared by a process comprising a step of reducing the moisture content from cyclophosphamide or liquid compositions of cyclophosphamide or both. The invention further relate to method of using such stable liquid formulations of cyclophosphamide for parenteral administration either as ready-to-use or ready-to-dilute for treating various cancer disorders.

9 Claims, No Drawings

STABLE LIQUID FORMULATIONS OF CYCLOPHOSPHAMIDE AND PROCESSES TO PREPARE THE SAME

This application is a Continuation-in-Part of PCT International Application No. PCT/IB2015/055285, filed Jul. 13, 2015, which claims the benefit of Indian Provisional Application Nos. 3454/CHE/2014, filed Jul. 11, 2014, and 5215/CHE/2014, filed Oct. 17, 2014, all of which are hereby incorporated by references in their entireties.

FIELD OF THE INVENTION

The present invention relates to stable liquid formulations of cyclophosphamide and processes to prepare the stable liquid formulations of cyclophosphamide. The present invention relates to stable pharmaceutical liquid formulations of cyclophosphamide comprising cyclophosphamide and at least one pharmaceutically acceptable excipient wherein moisture content of the liquid formulation is less than about 2.0% by weight. The invention further relates to stable liquid formulations of cyclophosphamide prepared by a process comprising a step of reducing the moisture content from cyclophosphamide or liquid compositions of cyclophosphamide or both. The invention further relate to method of using such stable liquid formulations of cyclophosphamide for parenteral administration either as ready-to-use or ready-to-dilute for treating various cancer disorders.

BACKGROUND OF THE INVENTION

Cyclophosphamide is alkylating agent indicated for treatment of a) Malignant Diseases, Hodgkin's disease, lymphocytic lymphoma, mixed-cell type lymphoma, histiocytic lymphoma, Burkitt's lymphoma; multiple myeloma, leukemias, mycosis fungoides, neuroblastoma, adenocarcinoma of ovary, retinoblastoma and breast carcinoma. b) Minimal Change Nephrotic Syndrome in Pediatric Patients (Only Oral dose is recommended).

Cyclophosphamide is a white crystalline powder with the molecular formula $C_7H_{15}Cl_2N_2O_2P.H_2O$ and a molecular weight of 279.1. Cyclophosphamide is soluble in water, saline, or ethanol. The chemical name for cyclophosphamide is 2-[bis(2-chloroethyl)amino]tetrahydro-2H-1,3,2-oxazaphosphorine 2-oxide monohydrate, The structure of cyclophosphamide monohydrate is represented by structure I.

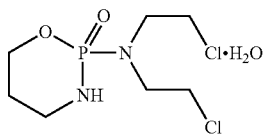

(I)

The cytotoxic action of nitrogen mustard is closely related to the reactivity of the 2-chloroethyl groups attached to the central nitrogen atom. Under physiological conditions, nitrogen mustards undergo intramolecular cyclization through elimination of chloride to form a cyclic aziridinium (ethyleneiminium) cation. This highly unstable cation is readily attacked on one of the carbon atoms of the three member aziridine ring by several nucleophiles, such as DNA guanine residues. This reaction releases the nitrogen of the alkylating agent and makes it available to react with the second 2-chloroethyl side chain, forming a second covalent linkage with another nucleophile, thus interfering with DNA replication by forming intrastrand and interstrand DNA crosslinks.

As on today, two forms exist for cyclophosphamide i.e. cyclophosphamide monohydrate form and anhydrous form. Cyclophosphamide monohydrate form is preferred for pharmaceutical processing, as the anhydrous form is highly unstable and readily picks up water to form the monohydrate when exposed to a relative humidity of about 20-30% or higher at about 25° C.

U.S. Pat. No. 3,018,302 disclose the cyclophosphamide as one of the novel cyclic phosphoric acid ester amides.

U.S. Pat. No. 4,775,533 cover the method for reconstituting dry fill cyclophosphamide for use in injections without having to resort to the expense of providing lyophilized products.

U.S. Pat. No. 5,036,060 discloses a stable lyophilizate of cyclophosphamide without the use of mannitol, by using the sodium chloride as the excipient.

U.S. Pat. No. 4,537,883 cover the lyophilized cyclophosphamide compositions for reconstitution with water to provide a solution for oral or parenteral administration.

US20070265213A1: Covers composition for treating metastatic breast cancer and ovarian cancer, wherein composition comprises cyclophosphamide, docetaxel, doxorubicin.

U.S. Pat. No. 8,399,434 cover compositions of cyclophosphamide with metalloporphyrin, wherein metalloprophyrin is included in an amount to enhance efficacy of cyclophosphamide.

As on today there are only solid formulations commercially available for cyclophosphamide. It is reported in the literature that nitrogen mustards exhibit poor stability in the aqueous solutions due to rapid degradation, this is further supported that as on today there are no liquid formulations commercially available. Cyclophosphamide is nitrogen mustard belonging to the chemical class of Oxazaphosphorins. Baxter has developed and launched Cytoxan (cyclophosphamide for injection USP). It is available as dry powder or lyophilized powders which on reconstitution with water are to be used immediately and when reconstituted with 0.9% sodium chloride injection it is stable up to 24 hours at room temperature and up to 6 days when refrigerated. The reconstituted solutions upon further dilution with sodium 0.45% sodium chloride injection it is stable up to 24 hours at room temperature and up to 6 days when refrigerated. Further when diluted with 5% dextrose injection or combination with 5% dextrose+0.9% sodium chloride injection it is stable up to 24 hours at room temperature and up to 36 hours when refrigerated. If it is reconstituted with water, the reconstituted solution is to be used immediately. Thus reconstituted and diluted solutions are stable only for a short period of time both at room temperature and refrigerated conditions and to be used within given shorter timelines.

Further, the nursing personnel must be aware of occupational exposure of potentially carcinogenic cytostatic agents during the preparation of reconstituted solutions, and contamination of the nursing staff should therefore be avoided as much as possible. As a dry powder or lyophilizate, the drug must be dissolved prior to removal for injection and then administered. Thus double handling of the drug. This necessitates additional entry to the vial with a syringe to add the solubilizing liquid vehicle. With each accession of the vial small quantities of the drug become airborne and this is known as aerosolization. Such added exposure requires particular precautions such as rubber gloves and masks. The Martindale Extra Pharmacopoeia. 28 Editions. Page 175, left column, report about this, the adverse effects of antineoplastic agents and recommends to handle these substances with great care and avoid contact with skin, eyes and not to be inhaled. But it has been reported that in during preparation of solutions of dry matter (sterile crystallizate, lyophilizate), however, an inhalation of such particles cannot be excluded with certainty. Furthermore, reconstitution introduces potential for dilution errors and may be necessary in some cases for a longer shaking period is required for solubilizing the drug completely.

Further the most common desirable solvent for lyophilization is water. The reactivity of most nitrogen mustards in aqueous solutions presents a challenge to the industrial scale manufacture of lyophilized products. Thus the manufacturing and administering solid forms of injectable drugs presents several problems. In addition to that, the lyophilization process is complex, costly and time consuming.

For the foregoing reasons, there is the need for "ready to use" or "ready to dilute" liquid formulations of cyclophosphamide. But for making such formulations of cyclophosphamide, suitable solvent system need to be identified in which cyclophosphamide does not degrade and remains stable during its shelf life.

There are prior art documents disclosing the liquid formulations of cyclophosphamide.

U.S. Pat. No. 4,952,575 cover storable solution of cyclophosphamide with 80-100% v/v of ethanol at a temperature from about 15° C. to about 40° C. These reported ethanolic or ethanolic-aqueous liquid formulations are highly concentrated with drug 10-70% w/v and ethanol aqueous solutions 80-100% v/v. The patent also discloses that trials carried out with solvents such as glycofurol, polyethylene glycol 300, polyethylene glycol 400, 1,2 propylene glycol, 1,3 butylene glycol.

U.S. Pat. No. 4,879,286 cover cyclophosphamide liquid formulation comprising 50 to 100% of an organic polyol and from about 0-50% water, particularly 80 percent propylene glycol and 20% polyethylene glycol giving greatest stability for the dissolved cyclophosphamide.

US20050272698A1 cover aqueous composition of oxazaphosphorin such as cyclophosphamide, Mesna and etherified ß-cyclodex.

EP1023075B1 describes liquid compositions of oxazaphosphorin with the chloride ion source, wherein chloride ion stabilize the oxazaphosphorin in aqueous solutions.

US20140005148A1 cover compositions of cyclophosphamide with poly ethylene glycol or propylene glycol or Glycerin or Dimethyl acetamide, polysorbate, polyethoxylated castor oil or combinations thereof. Further the application discloses that solvents like ethanol or other polar protic solvents are capable of nucleophilic attack on the carbon containing the chlorine atom in mustard moiety which will lead to formation of degradation products.

One of the commonly used techniques to avoid such instability in aqueous environment is use of non-aqueous solvent system for preparing the formulation. But it has been observed that some of the water sensitive drugs or excipients themselves have bound moisture causing instability. Due to this bound moisture the water sensitive drugs show instability even in the presence of non-aqueous solvent system. Hence these type of drugs possess challenge to the formulation scientist when preparing the formulation even in the non-aqueous solvent system. Thus it is important to remove the bound moisture or water content from the drug as well as from the excipients if required.

Even if we reduce water content from the drug or excipients individually there is high chance that during further process of preparing the formulation these drugs or excipients is exposed to environment and may pick up moisture. Hence removal of water content from drug or its liquid compositions and maintaining the water content throughout the process is critical in preparing the stable formulation.

However none of the above references disclose a stable formulations or compositions of cyclophosphamide which are stable for longer period of time.

Hence there is a still a need for the stable liquid formulations of cyclophosphamide and the processes to prepare such stable liquid formulations of cyclophosphamide. None of the above disclosed documents refer to the stable compositions and process to prepare the stable liquid formulations of water sensitive drugs such as cyclophosphamide which can meet the requirements for the commercial use. This need is fulfilled by the present invention.

The instant invention has resulted from work undertaken to ascertain if the stability of cyclophosphamide in solution can be improved thereby allowing the marketing of such formulations and obviating the aforementioned shortcomings of currently available dry powder mixtures and lyophilized compositions. In addition, the processes of the present invention used to prepare the stable liquid formulations of cyclophosphamide are simple, easy, cost effective, reproducible and quick to prepare.

SUMMARY OF THE INVENTION

The present invention relates to stable liquid formulations of cyclophosphamide processes to prepare such stable liquid formulations of cyclophosphamide. The invention relates to stable pharmaceutical liquid formulations of cyclophosphamide comprising cyclophosphamide and at least one pharmaceutically acceptable excipient wherein moisture content of the liquid formulation is less than about 2.0% by weight. The invention also relates to stable liquid formulations of cyclophosphamide prepared by a process comprising a step of reducing the moisture content from cyclophosphamide or liquid compositions of cyclophosphamide or both. The invention further relate to method of using such stable liquid formulations of cyclophosphamide for treating various cancer disorders.

In one of the embodiment the invention includes stable liquid formulations of cyclophosphamide comprising cyclophosphamide and at least one pharmaceutically acceptable excipient.

In a embodiment the invention relates to stable liquid formulations of cyclophosphamide comprising cyclophosphamide in pharmaceutically effective concentration and at least one pharmaceutically acceptable excipient.

In a embodiment the invention covers stable liquid formulations of cyclophosphamide wherein pharmaceutically effective concentration of cyclophosphamide is at least 0.1 g per mL In an embodiment the invention covers stable liquid formulations of cyclophosphamide wherein pharmaceutically effective concentration of cyclophosphamide is at least 0.5 g per mL In an embodiment the invention includes stable liquid formulations of cyclophosphamide prepared by a process comprising a step of reducing the moisture content from cyclophosphamide.

In another embodiment the invention includes process for preparing the stable liquid formulation of cyclophosphamide wherein process comprising the steps of a) reducing water content of cyclophosphamide by suitable drying methods.
b) preparing the bulk solution of cyclophosphamide by dissolving cyclophosphamide of step-a) in a suitable solvent.
c) filling bulk solution of step-b) in vials followed by stoppering and sealing.

In an embodiment the invention includes stable liquid formulations of cyclophosphamide wherein the moisture content of cyclophosphamide is reduced by selecting a suitable drying process selected from the group comprising of vacuum drying, lyophilization, solvent evaporation.

In one of the embodiment stable liquid formulations of cyclophosphamide prepared by removing the moisture content from cyclophosphamide is removed by vacuum drying.

In another embodiment the invention includes stable liquid formulations of cyclophosphamide prepared by a process comprising a step of reducing the moisture content from liquid compositions of cyclophosphamide.

Further embodiment includes stable liquid formulations of cyclophosphamide wherein the liquid formulations are prepared by a process comprising the steps of
a) preparing the bulk solution of cyclophosphamide by dissolving cyclophosphamide in a suitable solvent.
b) incubating the bulk solution of cyclophosphamide solution of step a) with adsorbents or mixture of adsorbents in suitable ratio for suitable period of time.
c) filtering the cyclophosphamide solution from step b) by using suitable filter followed by filling into vials, stoppering and sealing.

In an embodiment the invention includes stable liquid formulations of cyclophosphamide wherein the liquid formulations are prepared by a process comprising a step of reducing the moisture content from the liquid compositions of cyclophosphamide, wherein the process comprising the steps of
a) preparing the solution of cyclophosphamide by dissolving cyclophosphamide in a suitable solvent.
b) preparing at least one column by using suitable adsorbent or mixture of adsorbents. c) passing the cyclophosphamide solution from step a) through the column or series of columns of step b).
c) optionally filtering the solution through a suitable filter followed by filling into vials, stoppering and sealing.

In an embodiment the invention includes stable liquid formulations of cyclophosphamide wherein the liquid formulations are prepared by a process wherein the cyclophosphamide solution is passed through the column of adsorbents in a recirculation mode.

In an embodiment the invention includes stable liquid formulations of cyclophosphamide wherein the liquid formulations are prepared by a process wherein the cyclophosphamide solution is passed through the column of adsorbents at a flow rate ranging from about 0.1 mL/minute to about 5 L/minute.

In yet another embodiment the invention includes stable liquid formulations of cyclophosphamide prepared by a process comprising a step of reducing moisture content from both cyclophosphamide and liquid compositions of cyclophosphamide.

In an embodiment the invention includes stable liquid formulations of cyclophosphamide wherein the liquid formulations are prepared by a process comprising the steps of
a) reducing water content of cyclophosphamide by suitable drying methods.
b) preparing the solution of cyclophosphamide by dissolving cyclophosphamide of step a) in a suitable solvent.
c) preparing at least one column by using suitable adsorbent or mixture of adsorbents.
d) passing the cyclophosphamide solution from step b) through the column or series of columns of step c).
e) optionally filtering the solution through a suitable filter followed by filling into vials, stoppering and sealing.

In one of the embodiment the invention includes stable liquid formulations of cyclophosphamide wherein the suitable solvent selected from the group comprising of alcohol, polyethylene glycol, propylene glycol, dimethyl acetamide, glycerol, polysorbate 80, polyethoxylated castor oil or combinations thereof.

In an embodiment suitable solvent is alcohol or its combinations thereof.

In an embodiment the suitable solvent is ethanol or its combinations.

In a embodiment the invention includes stable liquid formulations of cyclophosphamide wherein the moisture content from liquid compositions of cyclophosphamide is reduced by means of adsorbents selected from the group comprising of molecular sieves, silica gel, activated alumina, activated charcoal or mixtures thereof.

In an embodiment the invention includes molecular sieves as adsorbent.

In an embodiment the invention includes the weight ratio of cyclophosphamide bulk solution to adsorbent in the range of about 1:0.01 to about 1:50.

In an embodiment the invention includes the weight ratio of cyclophosphamide bulk solution to adsorbent in the range of about 1:0.05 to about 1:25.

In a embodiment the invention relates to a stable liquid formulations of cyclophosphamide bulk solution to adsorbent in the range of about 1:0.1 to 1:10.

In an embodiment the invention includes liquid formulations of cyclophosphamide, wherein moisture content of liquid formulation is less than about 5% by weight of the composition.

In an embodiment the invention includes liquid formulations of cyclophosphamide, wherein moisture content of liquid formulation is less than about 2% by weight of the composition.

In an embodiment the invention includes liquid formulations of cyclophosphamide, wherein moisture content of liquid formulation is less than about 2% by weight of the composition when stored at 2-8° C. for at least 6M In an embodiment the invention relates to stable liquid formulations of cyclophosphamide wherein levels of impurity A in the formulation is less than about 1.5% by weight of label content of cyclophosphamide or its hydrate.

In an embodiment the invention relates to stable liquid formulations of cyclophosphamide wherein levels of impurity B in the formulation is less than about 1.5% by weight of label content of cyclophosphamide or its hydrate.

In an embodiment the invention relates to stable liquid formulations of cyclophosphamide wherein levels of impurity D in the formulation is less than about 1.5% by weight of label content of cyclophosphamide or its hydrate.

In an embodiment the invention relates to stable liquid formulations of cyclophosphamide wherein levels of specified impurity at 0.21 RRT in the formulation is less than about 1.5% by weight of label content of cyclophosphamide or its hydrate.

In an embodiment the invention relates to stable liquid formulations of cyclophosphamide wherein levels of specified impurity at 0.55 RRT in the formulation is less than about 2.5% by weight of label content of cyclophosphamide or its hydrate.

In an embodiment the invention relates to stable liquid formulations of cyclophosphamide wherein levels of specified impurity at 0.75 RRT in the formulation is less than about 2.5% by weight of label content of cyclophosphamide or its hydrate.

In one of the embodiment the invention relates to stable liquid formulations of cyclophosphamide wherein the total impurities are less than about 6% after storage at 2-8° C. for at least 6 months.

In one of the embodiment the invention includes stable liquid formulations of cyclophosphamide wherein the liquid formulations are prepared by a process comprising the steps of
a) preparing the bulk solution of cyclophosphamide by dissolving cyclophosphamide in ethanol
b) incubating the bulk solution of cyclophosphamide of step a) with molecular sieves until the moisture content of the solution is less than about 2.0% by weight of the composition.
c) filtering the cyclophosphamide solution from step b) by using suitable filter.

In an embodiment the invention includes stable liquid formulations of cyclophosphamide wherein the liquid formulations are prepared by a process comprising the steps of
  a) preparing the bulk solution of cyclophosphamide by dissolving cyclophosphamide in ethanol.
  b) preparing the column by using suitable molecular sieves.
  c) passing the cyclophosphamide solution from step a) through the column of step b) in a recirculation mode until moisture content of the formulation is less than about 2.0% by weight of the composition.
  d) optionally filtering the solution through a suitable filter.

In one of the embodiment the invention includes stable liquid formulations of cyclophosphamide wherein the liquid formulation is intended for parenteral administration.

In an embodiment the invention includes stable liquid formulations of cyclophosphamide wherein the liquid formulation is ready-to-use formulation.

In an embodiment the invention includes stable liquid formulations of cyclophosphamide wherein the liquid formulation is ready-to-dilute formulation.

In an embodiment the invention relates to methods of using stable liquid formulations of cyclophosphamide in treating various cancers.

DETAILED DESCRIPTION OF THE INVENTION

The present invention relates to stable liquid formulations of cyclophosphamide and processes to prepare the stable liquid formulations of cyclophosphamide. The invention relates to stable pharmaceutical liquid formulations of cyclophosphamide comprising cyclophosphamide and at least one pharmaceutically acceptable excipient wherein moisture content of the liquid formulation is less than about 2.0% by weight. The invention also relates to stable liquid formulations of cyclophosphamide prepared by a process comprising a step of reducing the moisture content from cyclophosphamide or liquid compositions of cyclophosphamide or both. The invention further relate to method of using such stable liquid formulations of cyclophosphamide for treating various cancer disorders.

The various cancer disorders according to the invention includes Malignant lymphomas (Stages III and IV of the Ann Arbor staging system), Hodgkin's disease, lymphocytic lymphoma (nodular or diffuse), mixed-cell type lymphoma, histiocytic lymphoma, Burkitt's lymphoma; Multiple myeloma; Leukemias: Chronic lymphocytic leukemia, chronic granulocytic leukemia (it is usually ineffective in acute blastic crisis), acute myelogenous and monocytic leukemia, acute lymphoblastic (stem-cell) leukemia in children (cyclophosphamide given during remission is effective in prolonging its duration); Mycosis fungoides (advanced disease); Neuroblastoma (disseminated disease); Adenocarcinoma of the ovary; Retinoblastoma; Carcinoma of the breast; biopsy proven "minimal change" nephrotic syndrome in children.

The liquid formulations according to the invention possess number of advantages as compared to solutions prepared from sterile powders or lyophilizate immediately before use, they are a) less likely to be contaminated by particles or microbes b) render the dissolution step superfluous and may be used immediately; c) contribute to the safety of the nursing staff who is handling the reconstitution or administration of the drug and are more economical to prepare.

The term "cyclophosphamide" is intended to include any of the alternative forms in which cyclophosphamide can be administered such as salts, esters, anhydrous, hydrates such as monohydrate or dihydrate, solvates, crystalline or amorphous polymorphs, racemic mixtures, enantiomeric isomers and so on unless it is restricted to specific property for example cyclophosphamide with moisture content less than 5% by weight.

The terms 'stable' or 'stability' as used herein relate to both physical and chemical stability, wherein cyclophosphamide can be stored for commercially significant periods, such as at least 3 months, 6 months, 1 year, or 2 years or 3 years, without significant physical instability (description, clarity etc) and chemical degradation. The stable may represent stability when stored at 2-8° C. or at ambient conditions (e.g. 25° C.) or elevated temperatures (e.g. 40° C.). Percent degradation may be determined by analyzing for impurities by suitable analytical method.

The term "pharmaceutically acceptable" refers to ingredients that are useful for preparing pharmaceutical compositions, and that is considered to be generally safe, non-toxic and neither biologically nor otherwise undesirable, and includes those ingredients acceptable for veterinary use as well as human pharmaceutical use.

The term "substantial" as used to describe percentage of hydrates or solvates of cyclophosphamide in the formulation includes at least about 90%, or at least about 95%, or at least about 99% anhydrous form.

The term "moisture content" or water content or bound water refer to the water content of the drug or tis formulation and are synonymously used in the present invention. The moisture content may be bound or in unbound form.

The term "ready to use" or "RTU" composition is a stable formulations of cyclophosphamide which are ready for administration which may be oral or parenteral administration.

The term "ready-to-dilute" or RTD composition is a stable liquid formulations that are to be diluted with the suitable diluent further for oral or parenteral administration. Suitable diluents may include sterile water for injection, 0.9% sodium chloride, 0.45% sodium chloride, 5% dextrose or combinations thereof.

The term "sterile" composition is one in which essentially all forms of microbial life has been destroyed by an appreciable amount to meet the sterilization criteria outlined in the United States Pharmacopoeia.

The term "incubation" denotes that cyclophosphamide solution is in contact with the adsorbent for certain period of time or adsorbents are immersed in bulk solution of drug for certain period of time.

The term "adsorbent" includes any substance used to remove or reduce moisture or water content from any other substance or its compositions. Substance may be drug or excipient or mixtures thereof. Sometimes adsorbents also refer to dessicants.

The term "pharmaceutically effective concentration" refers to any concentration of the drug showing its therapeutic effect.

The terms "anhydrous alcohol" or dehydrated alcohol" or "absolute alcohol" are used synonymously.

The bulk solution of the drug as discussed in this application refers to any solution prepared by dissolving drug in a suitable solvent optionally with stirring.

The term "composition" in the present invention refers to combination of drug along with at least one pharmaceutically acceptable excipient and used in preparing pharmaceutical formulations with no specific limitations. The liquid compositions refer to the compositions in the liquid form.

The term "formulation" refers to pharmaceutical dosage forms containing compositions of cyclophosphamide. The pharmaceutical formulations of the present invention can be prepared as solutions or suspensions or emulsion or dispersions or elixirs and so on presented in glass ampoules or glass vials or any suitable devices.

The formulations of the present invention are particularly suitable for use in parenteral administration, but it will be understood that the solutions may have alternative uses. For example, they may be used as intermediates in the preparation of other pharmaceutical dosage forms. Similarly, they may have other routes of administration including oral or intranasal or inhalation. Injectable formulations may take any route including intramuscular, intravenous or subcutaneous or intrathecal, intraarterial and so on.

Injectable formulations are frequently formulated as aqueous solutions, in which water is the primary excipient. Injectable formulations can be prepared in conventional forms, either as liquid solutions or suspensions, solid forms suitable for solubilization or suspension in liquid prior to injection, or as emulsions. Sterile injectable formulations can be prepared according to techniques known in the art using suitable carriers, dispersing or wetting agents, and suspending agents. The injectable formulations may be sterile injectable solutions or suspensions in a nontoxic, parenteral acceptable diluent or solvent. Injectable formulations can be used as ready-to-use or ready-to-dilute compositions.

Cyclophosphamide being nitrogen mustard exhibit poor stability in aqueous solutions due to rapid degradation. Mainly for this reason cyclophosphamide has historically been compounded as a sterile dry powder mixture of cyclophosphamide monohydrate for reconstitution with water for Injection or as the lyophilized solid with mannitol excipient for reconstitution with water for Injection. It has been also observed that the reconstituted solutions with water are to be administered immediately. Both procedures require costly, extensive processing in production and time-consuming hazardous handling in preparation or reconstitution. Additionally, both compositions lead to costly waste due to very short shelf-life of the reconstituted solutions. Consequently, portions not used immediately must be discarded.

Due to inherent instability of cyclophosphamide in aqueous solutions, different non-aqueous solvents have been explored to prepare the liquid formulation. With the use of non-aqueous solvents, the stability of cyclophosphamide was improved when compared to aqueous preparations but it was not promising on stability. Even in presence of non-aqueous solvents (which contribute to very less quantity of moisture or water content) also cyclophosphamide was not that stable. It was understood that probably the bound water of cyclophosphamide monohydrate (approximately 6.25%) may be responsible for hydrolytic degradation cyclophosphamide in non-aqueous solvent such as anhydrous ethanol. There are different techniques to remove or reduce water from the cyclophosphamide such as lyophilization, vacuum drying, solvent evaporation, adsorbents such as molecular sieve, silica gel, activated alumina, activated charcoal etc.

In one of the embodiment the invention includes stable liquid formulations of cyclophosphamide comprising cyclophosphamide and at least one pharmaceutically acceptable excipient.

In a embodiment the invention relates to stable liquid formulations of cyclophosphamide comprising cyclophosphamide in pharmaceutically effective concentration and at least one pharmaceutically acceptable excipient.

In an embodiment the invention relates to stable liquid formulations of cyclophosphamide wherein cyclophosphamide used in the formulation is substantially in anhydrous form.

In an embodiment the invention includes the stable liquid formulations of cyclophosphamide comprising cyclophosphamide with moisture content less than about 5% by weight of the composition or is substantially anhydrous form.

In an embodiment the invention includes the stable liquid formulations of cyclophosphamide comprising cyclophosphamide with moisture content less than about 2% by weight of the composition.

In an embodiment the invention includes the stable liquid formulations of cyclophosphamide comprising cyclophosphamide with moisture content less than about 2% by weight of the composition when stored at 2-8° C. for at least 6M.

In an embodiment the invention covers stable liquid formulations of cyclophosphamide wherein pharmaceutically effective concentration of cyclophosphamide is at least 0.1 g per mL.

In an embodiment the invention covers stable liquid formulations of cyclophosphamide wherein pharmaceutically effective concentration of cyclophosphamide is at least 0.5 g per mL.

It has been observed that when the bound water was reduced from cyclophosphamide monohydrate by subjecting to vacuum drying, the cyclophosphamide with reduced water content showed better stability than its monohydrate form in anhydrous ethanol. This further confirms that the bound water of cyclophosphamide monohydrate may be responsible for degradation.

In an embodiment the invention includes stable liquid formulations of cyclophosphamide prepared by a process comprising a step of reducing the moisture content from cyclophosphamide.

In another embodiment the invention includes process for preparing the liquid formulations of cyclophosphamide wherein process comprising the steps of
  a) reducing water content of cyclophosphamide by suitable drying methods.

b) preparing the solution of cyclophosphamide by dissolving cyclophosphamide with reduced water content of step-a) in a suitable solvent. Optionally the solution is filtered through a suitable filter.

c) filling bulk solution of step-b) in vials followed by sealing.

In an embodiment the invention includes stable liquid formulations of cyclophosphamide wherein the moisture content of cyclophosphamide is reduced by selecting a suitable drying process selected from the group comprising of vacuum drying, lyophilization, solvent evaporation.

In one of the embodiment stable liquid formulations of cyclophosphamide prepared by removing the moisture content from cyclophosphamide by vacuum drying.

In another embodiment the invention includes stable liquid formulations of cyclophosphamide prepared by a process comprising a step of reducing the moisture content from liquid compositions of cyclophosphamide.

In another embodiment the invention includes stable liquid formulations of cyclophosphamide prepared by a process comprising a step of reducing the moisture content from both cyclophosphamide and the liquid compositions of cyclophosphamide.

In an embodiment the invention includes stable liquid formulations of cyclophosphamide wherein the moisture content from liquid compositions of cyclophosphamide is reduced by means of adsorbents selected from the group comprising of molecular sieves, silica gel, activated alumina, activated charcoal.

In an embodiment the invention includes process of reducing the moisture content from liquid formulations of cyclophosphamide by using molecular sieves.

Molecular sieve are pelleted, beaded and powdered material, made from three dimensional materials. A molecular sieve is a material with very small holes of precise and uniform size. These holes are small enough to block large molecules while allowing small molecules to pass. The small molecules are efficient to pass through the pores and when activated they becomes a powerful adsorbents in a wide range of operating conditions with a strong absorption ability with water, hydrogen, oxygen, carbon dioxide and other polar molecules. The term "activated" with respect to adsorbents refer to the process wherein the molecular sieves are heated to certain temperature for certain period of time. For example molecular sieves when heated at 120° C. for about 12 hours may be referred to as activated molecular sieves.

Molecular sieves are used as adsorbent for gases and liquids. Molecules small enough to pass through the pores are adsorbed while larger molecules are not. It is different from a common filter in that it operates on a molecular level and traps the adsorbed substance. For instance, a water molecule may be small enough to pass through the pores while larger molecules are not, so water is forced into the pores which act as a trap for the penetrating water molecules, which are retained within the pores. Because of this, they often function as a desiccant. A molecular sieve can adsorb water up to 22% of its own weight. The principle of adsorption to molecular sieve particles is somewhat similar to that of size exclusion chromatography, except that without a changing solution composition, the adsorbed product remains trapped because, in the absence of other molecules able to penetrate the pore and fill the space, a vacuum would be created by desorption.

There are different types of molecular sieves available. Molecular sieves can be microporous, mesoporous, or macroporous material.

Microporous (<2 nm) eg: Zeolites (aluminosilicate minerals; Porous glass; Active carbon: Clays such as Montmorillonite, Halloysite etc Mesoporous material (2-50 nm) eg: Silicon dioxide (used to make silica gel).

Macroporous material (>50 nm) eg: Mesoporous silica

Further there are different models available for molecular sieves based on their adsorption capabilities including pore diameter, bulk density, adsorbed water etc. For example:

13× and 10× Molecular Sieves (Beads, Pellets and Powder)

3A Molecular Sieves (Beads, Pellets and Powder)

4A Molecular Sieves (Beads, Pellets and Powder)

5A Molecular Sieves (Beads, Pellets and Powder)

Among the available models of molecular sieves, type 3A molecular sieve was used for removing or reducing water from liquid formulation considering its unique pore size.

By using molecular sieves the water can be removed or reduced by different methods such as Static process wherein adsorbent or mixture of adsorbents in certain weight ratio were incubated or immersed in the cyclophosphamide bulk solution.

Dynamic process wherein the bulk solution of cyclophosphamide was passed through the column or series of columns containing adsorbent or mixture of adsorbents. The dynamic process can further be in a recirculation method wherein the bulk solution was continuously recirculated through the column using peristaltic pump. Recirculation will increase the efficiency of absorption.

In one of the embodiment the invention includes the stable liquid formulations of cyclophosphamide wherein weight ratio of cyclophosphamide bulk solution to adsorbent is 1:0.01 to 1:50.

In an embodiment the invention includes the stable liquid formulations of cyclophosphamide wherein weight ratio of cyclophosphamide bulk solution to adsorbent is 1:0.05 to 1:25.

In one of the embodiment the invention includes the stable liquid formulations of cyclophosphamide wherein weight ratio of cyclophosphamide bulk solution to adsorbent is 1:0.1 to 1:10.

In one of the embodiment the invention includes the stable liquid formulations of cyclophosphamide wherein weight ratio of cyclophosphamide bulk solution to adsorbent is 1:0.1 to 1:5.

In one of the embodiment the invention includes the stable liquid formulations of cyclophosphamide wherein weight ratio of cyclophosphamide bulk solution to adsorbent is 1:0.1 to 1:2

In one of the embodiment the adsorbent is molecular sieves.

In another embodiment the invention includes the stable liquid formulations of cyclophosphamide, wherein moisture content of liquid formulation is less than about 5% by weight of the composition.

In another embodiment the invention includes the stable liquid formulations of cyclophosphamide, wherein moisture content of liquid formulation is less than about 2% by weight of the composition.

In another embodiment the invention includes the stable liquid formulations of cyclophosphamide, wherein moisture content of liquid formulation is less than about 1% by weight of the composition.

In one of the embodiment the invention includes the pharmaceutical liquid formulations of cyclophosphamide comprising cyclophosphamide and at least one pharmaceutically acceptable excipient.

In an embodiment the invention includes stable liquid formulations of cyclophosphamide comprising cyclophosphamide and at least one pharmaceutically acceptable excipient is non-aqueous solvent.

The various non-aqueous solvents suitable for the formulations of the present invention include but not limited to alkyl alcohols, for example, ethanol/anhydrous ethanol/dehydrated alcohol/absolute alcohol, ethylene glycol, propylene glycol, butylene glycol, glycerin or glycerol, polysorbates, for example TWEEN 20, TWEEN 40, and TWEEN 80, and cyclodextrins (such as hydroxypropyl-.beta.-cyclodextrin), polyalkylene glycols, such as polyethylene glycol, polypropylene glycol, and polybutylene glycol, diemthyl acetamide, niacinamide, a diol such as a straight chain, branched or cyclic aliphatic diol, a triol such as straight chain, branched or cyclic aliphatic triol, a polyoxyethylene ether and a polyethylene glycol ether.

The aliphatic diol may have either a straight chain or a branched chain and have 2-20 carbon atoms. Exemplary suitable aliphatic diols include 1,2-propane diol, 1,3-propane diol, 1,4-butane diol, 1,5-pentane diol and its higher aliphatic homologs and their positional isomers. The aliphatic cyclic diol may have from 5 to 20 carbon atoms. Exemplary suitable aliphatic cyclic diols include 1,2-cyclopentane diol, 1,2-cyclohexane diol and its higher aliphatic homologs and their positional isomers. The aliphatic triol may have from 3 to 20 carbon atoms and may have a straight chain or a branched chain Exemplary suitable aliphatic triols include glycerin (glycerol) and its higher aliphatic homologs and their positional isomers like butane 1,2,3-triol, 1,3,5-pentane triol. The aliphatic cyclic triol may have from 5 to 20 carbon atoms. Exemplary aliphatic cyclic triols include cyclohexane triol, cycloheptanetriol its higher aliphatic homologs and all their positional isomers. The polyoxy ethylene ether, exemplary polyoxyethylene ethers include polysorbate-20 (Tween-20), polysorbate-40 (Tween-40), polysorbate-60 (Tween-60), and polysorbate-80 (Tween-80). The polyethylene glycol ether, exemplary polyethylene glycol ethers include polyethoxylated castor oil, such as Cremophor® and other poly ethers in that class.

In an embodiment the invention includes stable liquid formulations of cyclophosphamide wherein excipient is at least one non-aqueous solvent selected from the group comprising ethanol, propylene glycol, polyethylene glycol, dimethyl acetamide, glycerol, polysorbate 80, polyethoxylated castor oil or combinations thereof.

In an embodiment the invention relates to stable liquid formulations of cyclophosphamide wherein non-aqueous solvent is ethanol.

In an embodiment the invention relates to stable liquid formulations of cyclophosphamide wherein non-aqueous solvent is anhydrous ethanol.

In another embodiment the invention includes stable liquid formulations of cyclophosphamide wherein ethanol is in the concentration of 10 to 100% by weight of the composition.

In another embodiment the invention includes stable liquid formulations of cyclophosphamide wherein non-aqueous solvent system is combination of ethanol such as glycerol with ethanol or propylene glycol with ethanol or polyethylene glycol with ethanol or polysorbate with ethanol or cremophor with ethanol.

In an embodiment the invention includes pharmaceutical stable liquid formulations of cyclophosphamide, wherein non aqueous solvent or combination of non-aqueous solvents are present in the formulation in a range from about 10 to 100% by weight.

In one of the embodiment the invention includes stable liquid formulations of cyclophosphamide wherein the liquid formulations are prepared by a process comprising the steps of
  a) preparing the bulk solution of cyclophosphamide by dissolving cyclophosphamide in ethanol
  b) incubating the bulk solution of cyclophosphamide of step a) with molecular sieves until the moisture content of the solution is less than about 2.0% by weight of the composition.
  c) filtering the cyclophosphamide bulk solution from step b) by using suitable filter followed by filling into vials, stoppering and sealing.

In an embodiment the invention includes stable liquid formulations of cyclophosphamide wherein the liquid formulations are prepared by a process comprising steps of
  a) preparing the bulk solution of cyclophosphamide by dissolving cyclophosphamide in ethanol.
  b) preparing the column by using suitable grade of molecular sieves.
  c) passing the cyclophosphamide solution from step a) through the column of step b) in a recirculation mode until moisture content of the formulation is less than about 2.0% by weight of the composition.
  d) optionally filtering the solution through a suitable filter then followed by filling into vials, stoppering and sealing.

In an embodiment the invention includes stable liquid formulations of cyclophosphamide wherein the liquid formulations are prepared by a process comprising the steps of
  a) reducing water content of cyclophosphamide by suitable drying methods.
  b) preparing the bulk solution of cyclophosphamide by dissolving cyclophosphamide of step a) in a suitable solvent.
  c) preparing at least one column by using suitable adsorbent or mixture of adsorbents. d) passing the cyclophosphamide solution from step b) through the column or series of columns of step c).
  d) optionally filtering the solution through a suitable filter followed by filling into vials, stoppering and sealing.

In an embodiment the invention includes stable liquid formulations of cyclophosphamide, wherein the cyclophosphamide solution is prepared by dissolving cyclophosphamide in suitable solvent by stirring at 50 to 2000 rpm speed.

In one of the embodiment the invention includes stable liquid formulations of cyclophosphamide wherein the liquid formulations are prepared by a process which is under continuous nitrogen purging.

In an embodiment the invention includes stable liquid formulations of cyclophosphamide prepared by dissolving cyclophosphamide in a suitable solvent purged with nitrogen followed by filling into glass vial, stoppered and sealing.

In one of the embodiment the invention includes stable liquid formulations of cyclophosphamide wherein the liquid formulation is intended for parenteral administration.

In an embodiment the invention includes stable liquid formulations of cyclophosphamide wherein the liquid formulation is ready-to-use formulation.

In an embodiment the invention includes stable liquid formulations of cyclophosphamide wherein the liquid formulation is ready-to-dilute formulation.

From the degradation data it has been observed that the degradants are formed by attack on the carbon containing chlorine atom. By including chloride ion source in the formulation the formation of degradants by attack on the carbon atom can be minimized. Suitable chloride ion source includes sodium chloride, potassium chloride, hydrochloric acid or any other source of chloride ion that is sufficiently soluble in the chosen formulation solvent. In an embodiment the chloride ion source is present in the range of about 0.01% to about 15% w/w of the formulation.

However chloride ion sources for example sodium chloride or potassium chloride etc. is soluble in water and has limited solubility in non-aqueous solvents. To stabilize cyclophosphamide chloride ion source should be in solubilized form. Hence while preparing the stable liquid formulation of cyclophosphamide with chloride ion source, identification of suitable non aqueous solvent wherein chloride ion is in solubilized form to stabilize the cyclophosphamide is critical and important.

In an embodiment the invention includes the process of preparing the liquid formulations wherein process comprising the steps of
a) preparing the bulk solution of cyclophosphamide by dissolving cyclophosphamide in nitrogen purged first non-aqueous solvent.
b) dissolving chloride ion source in nitrogen purged second non-aqueous solvent.
c) mixing step a) and step b)
d) filling the bulk solution into glass vials followed by stoppering and sealing.

In one of the embodiment the invention relates to stable ready to use injectable liquid formulations of cyclophosphamide, wherein formulations comprise cyclophosphamide and non-aqueous solvent or solvent system such that the chloride ion source is in solubilized form.

In an embodiment the invention includes the stable ready to use injectable liquid formulations wherein formulation comprise non-aqueous solvent or solvent system that is capable of keeping chloride ion source in solubilized form is glycerol or propylene glycol or combination thereof.

The pH of the non-aqueous liquid plays a crucial role in the stability of the nitrogen mustard formulation. Protonation of the nitrogen in the mustard moiety avoids the formation of an aziridine ring, which is highly unstable and can result in unacceptable levels of degradation of the nitrogen mustard. An acidic pH is required to maintain the protonated state of the nitrogen in the mustard moiety. In an embodiment, the pH of the formulation is in a range between about pH 3 to about pH 9.

In an embodiment the invention includes the liquid formulations of cyclophosphamide with at least one pH adjusting agents or at least one buffering agent The pH-adjusting agents may include pharmaceutically acceptable acids, bases, or buffering agents. For example, the acids may include, but are not limited to, one or more inorganic mineral acids such as hydrochloric, hydrobromic, sulfuric, phosphoric, nitric, and the like; or one or more organic acids such as acetic, succinic, tartaric, ascorbic, citric, fumaric, oxalic, maleic acie, adipic acid, glutamic, benzoic, methanesulphonic, ethanesulfonic, trifluoroacetic, hydroxy acid or alpha hydroxy acids and the like. The bases may be one or more inorganic bases or organic bases, including, but not limited to, alkaline carbonate, alkaline bicarbonate, alkaline earth metal carbonate, alkaline hydroxide, alkaline earth metal hydroxide or amine such as ethanolamine. For example, the inorganic or organic base may be an alkaline hydroxide such as lithium hydroxide, potassium hydroxide, cesium hydroxide, sodium hydroxide or the like; an alkaline carbonate such as calcium carbonate, sodium carbonate or the like; or an alkaline bicarbonate such as sodium bicarbonate or the like; the organic base may also be sodium acetate Buffering agents may comprise pharmaceutically acceptable reagents or components that contribute to maintaining pH between 3 to 9. Suitable buffering agents include but not limited to ascorbate, lactobionate, gentisate, succinate, .alpha.-lipoic acid, maleate, chloroacetate, citrate, bicarbonate, tartrate, glycylglycine, formate, benzoate, phosphate, citrate, lactate, acetate, propionate, pyridine, piperazine, pyrophosphate, histidine, 2-(N-morpholino)ethanesulfonic acid ("MES"), cacodylic acid, (bis(2-hydroxyethyl)-iminotris(hydroxymethyl)-methane) ("bis-TRIS"), bicarbonate, or a combination of these buffering agents Additional excipients that can be included in the liquid formulations of the present invention include antioxidants, preservatives, polymers, sugars or polyols or combination thereof. Suitable antioxidants include but not limited to butylated hydroxytoluene, butylated hydroxy anisole, alpha.-tocopherol, citric acid, ascorbic acid, monothiogleycerol, sodium sulfite, sodium metabisulfite, thymol, propyl gallate, histidine, methionine and combinations thereof. The antioxidant may be present at a range of about 0.01% w/w to about 10% w/w of the formulation.

Suitable buffering agent include but not limited to acetate, tartrate, ascorbate, lactobionate, gentisate, succinate, lactate, α-lipoic acid or any combinations thereof. Suitable polymers include poloxamers, hydroxyethyl starch, polyvinyl pyrrolidone or combination thereof. Suitable preservatives include but not limited to methyl-, ethyl- and propyl parabens or any combination thereof. Suitable polyols include but not limited to sucrose, dextrose, dextrin, propylene glycol, sorbitol, glycerol or any combinations thereof.

In various embodiments the composition may further include one of more tonicity modifying agents such as sodium chloride, dextrose, boric acid, sodium tartrate, propylene glycol, polyols (such as mannitol and sorbitol), or other inorganic or organic solutes. inorganic salts, organic salts or combination thereof. Apart from sodium chloride, the other inorganic salts may comprise potassium chloride, magnesium chloride, calcium chloride and the organic salts may comprise conjugate base of trifluoroacetic acid.

As discussed above, cyclophosphamide is highly unstable in presence of moisture/water content and/or temperature. From the forced degradation data of cyclophosphamide, it has been observed that six known impurities namely Impurity A, B, D and three unknown specified impurities are obtained under different stressed conditions as shown below
a) Impurity A is formed in acidic conditions. Impurity A, chemically Bis (2-Chloroethyl) amine hydrochloride and represented by structure II.
b) Impurity B is formed due to basic hydrolysis. Impurity B, chemically 3-(2-Chloroethyl)-2-oxo2-hydroxy-1,3, 6,2-oxadiazaphosphone and represented by structure III.
c) Impurity D chemically 3-[2-(2-chloroethylamino) ethylamino] propyldihydrogen phosphate dihydrochloride and represented by structure IV.

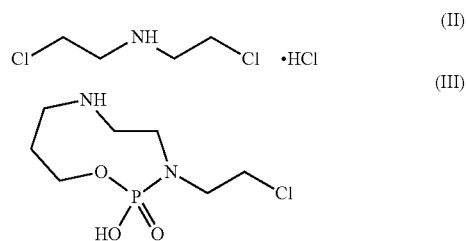

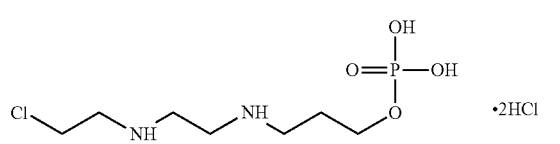

d) Specified impurity at 0.21 RRT.
e) Specified impurity at 0.55 RRT.
f) Specified impurity at 0.75 RRT.

In an embodiment the invention relates to stable liquid formulations of cyclophosphamide wherein levels of impurity A in the formulation is less than about 1.5% by weight of label content of cyclophosphamide or its hydrate.

In an embodiment the invention relates to stable liquid formulations of cyclophosphamide wherein levels of impurity B in the formulation is less than about 1.5% by weight of label content of cyclophosphamide or its hydrate.

In an embodiment the invention relates to stable liquid formulations of cyclophosphamide wherein levels of impurity D in the formulation is less than about 1.5% by weight of label content of cyclophosphamide or its hydrate.

In an embodiment the invention relates to stable liquid formulations of cyclophosphamide wherein levels of specified impurity at 0.21 RRT in the formulation is less than about 1.5% by weight of label content of cyclophosphamide or its hydrate.

In an embodiment the invention relates to stable liquid formulations of cyclophosphamide wherein levels of specified impurity at 0.55 RRT in the formulation is less than about 2.5% by weight of label content of cyclophosphamide or its hydrate.

In an embodiment the invention relates to stable liquid formulations of cyclophosphamide wherein levels of specified impurity at 0.75 RRT in the formulation is less than about 2.5% by weight of label content of cyclophosphamide or its hydrate.

In an embodiment the invention relates to stable liquid formulations of cyclophosphamide wherein total drug related impurities in the formulation is less than about 6% by weight of label content of cyclophosphamide or its hydrate.

In one of the embodiment the invention relates to stable liquid formulations of cyclophosphamide wherein the total impurities are less than about 6% after storage at 2-8° C. for at least 3 months or at least 6 months.

The moisture content from the cyclophosphamide can be removed by applying any suitable drying technique such as lyophilization, vacuum drying, solvent evaporation, use of adsorbents such as molecular sieves, activated charcoal, activated alumina, silica gel and so on.

In an embodiment the invention includes pharmaceutical liquid formulations of cyclophosphamide, wherein cyclophosphamide is at the pharmaceutically effective concentration in the range of about 0.1 mg/mL to about 5 g/mL.

In an embodiment the invention includes pharmaceutical liquid formulations of cyclophosphamide, wherein cyclophosphamide is at the pharmaceutically effective concentration of at least 0.1 g/ml.

In an embodiment the invention includes pharmaceutical liquid formulations of cyclophosphamide, wherein cyclophosphamide is at the pharmaceutically effective concentration of at least 0.5 g/ml.

To prepare the pharmaceutical dosage form, the pharmaceutical formulation can be packaged in the container by any suitable method known in the art.

The solutions are often required to filter to remove the unwanted particles from it. For this a suitable filters such as PVDF filters of size 0.2 micron may be used.

In embodiments, the invention provides methods of filling containers that contain a solution of cyclophosphamide or salts or hydrates, comprising: a) providing one or more open containers; b) filing the containers with a solution of cyclophosphamide optionally in an aseptic environment; c) sealing the filled containers; and d) sterilizing the sealed, filled containers.

The liquid compositions of cyclophosphamide can be contained within a sealed container. More preferably, the container is provided with an opening and means for aseptically sealing the opening, e.g, such that the sealed container is fluidly sealed or the sealed opening is substantially impermeable to atmospheric gases, moisture, pathogenic microorganisms or the like. The container can be constructed any suitable material such as, for example glass, polypropylene, polyethylene terephthalate, and the like. In a preferred embodiment the container is constructed of glass. Suitable glass vials include molded and tubing glass vials such as, for example, Type I molded glass vials, and the like.

A suitable means for sealing the container can include, for example, a stopper, a cap, a lid, a closure, a covering which fluidly seals the container, or the like. The means for sealing the container are not limited to separate closures or closure devices. In a embodiment, the means for aseptically sealing the container includes a stopper such as, for example, a stopper that is configured to fluidly seal the opening. Suitable stoppers include conventional medical grade stoppers which do not degrade or release significant amounts of impurities. Some of the stopper materials include silicone rubber, Teflon coated stoppers, slotted bromobutyl rubber, etc.

Optionally, an outer seal is provided which covers and entirely surrounds the stopper. The outer seal can be constructed of any suitable material. When an outer seal is used, it is preferably fitted with a lid that can be easily manually removed to provide access to the stopper. Suitable outer seals can include, for example, Flip-off Aluminum/Polypropylene Seals. Such seals include an outer rim made of a suitable material, such as aluminum, that entirely surrounds the lateral edge of the stopper and further include a lid (typically polypropylene or other suitable material) that entirely covers the upper surface of the stopper. The polypropylene lid can be "flipped" off e.g., by exerting upward pressure with a finger or thumb, to provide access to the stopper, e.g., so that it can be punctured with a hypodermic needle to withdraw the composition from the vial.

The other suitable devices for liquid formulations include but not limited to, pre-filled syringes or pen devices or auto-injectors and so on.

The invention includes use of packaging materials such as containers and closures of high-density polyethylene (HDPE), low-density polyethylene (LDPE) and or polypropylene and/or glass, glassine foil, polyvinyl chloride, polyvinylidene dichloride, etc.

In yet another embodiment the invention includes the methods of using the liquid formulations of cyclophosphamide in treating cancers. Various cancers include malignant lymphomas: Hodgkin's disease, lymphocytic lymphoma, mixed-cell type lymphoma, histiocytic lymphoma, Burkitt's lymphoma; multiple myeloma, leukemias, mycosis fungoides, neuroblastoma, adenocarcinoma of ovary, retinoblastoma, breast carcinoma. The formulations of the present invention may also be extended to treat nephrotic Syndrome in Pediatric Patients who failed to adequately respond to or are unable to tolerate adrenocorticosteroid Therapy.

Analytical Method:
1. Water content: Water content was estimated by karl fischer (KF) method wherein suitable quantity of methanol was taken in the flask and titrated with karl fischer reagent to neutralize the methanol. Then weighed quantity of the sample is added to the flask and titrated to the end point.
2. Impurities: The known impurities such as impurity A,B,D, unknown specified impurities, unknown impurities and the total impurities were estimated by the following analytical method:

Buffer: Potassium dihydrogen phosphate was taken in water and the pH adjusted to pH 7.0 with diluted sodium hydroxide solution followed by filtration through 0.45 μm filter.

Mobile Phase A: The buffer was used as mobile phase A.

Mobile phase B: The buffer and acetonitrile was mixed in 20:80 v/v ratios respectively.

Chromatographic Conditions:

Column: Waters symmetry shield RP-18 250×4.6 mm, 5 μm

Flow rate: 0.5 mL/min

Wavelength of detection: 195 nm

Column temperature: 25° C.±5° C.

Injection volume: 20 μL

Run time: 80 minutes

Diluent: HPLC Grade Water.

Gradient Program:

| Time (Minutes) | Mobile Phase-A % | Mobile Phase-B % |
|---|---|---|
| 0 | 100 | 0 |
| 10 | 100 | 0 |
| 40 | 50 | 50 |
| 55 | 20 | 80 |
| 65 | 20 | 80 |
| 70 | 100 | 0 |
| 80 | 100 | 0 |

Representative relative retention factor (RRF) and relative retention time (RRT) are represented as below:

| Name of the compound | RRT | RRF |
|---|---|---|
| Cyclophosphamide | 1.00 | 1.00 |
| Impurity A | 0.91 | 1.10 |
| Impurity B | 0.15 | 0.82 |
| Impurity D | 0.18 | 0.44 |
| Specified impurity at 0.21 | 0.21 | — |
| Specified impurity at 0.55 | 0.55 | — |
| Specified impurity at 0.75 | 0.75 | — |

The following examples further describe certain specific aspects and embodiments of the invention and demonstrate the practice and advantages thereof. It is to be understood that the examples are provided only for purposes of illustration and are not intended to limit the scope of the invention in any manner.

EXAMPLES

Comparative Example 1: Pharmaceutical Formulation of Cyclophosphamide Monohydrate [without Reducing the Moisture Content]

Composition:

| Ingredients | Quantity |
|---|---|
| Cyclophosphamide monohydrate | 500 mg |
| Anhydrous ethanol or dehydrated alcohol | qs to 1 mL |

Manufacturing Process:
1) Cyclophosphamide monohydrate was taken in vessel. 60% of dehydrated alcohol was added to vessel with continuous stirring at 300-400 rpm until clear solution was obtained.
2) Then remaining quantity of dehydrated alcohol was added to make up the volume 100% and stirred for about 10 minutes to obtain a clear homogeneous solution.
3) Bulk solution was filtered through 0.2μ filter and filtered solution was filled in 2 mL glass vial, stoppered and sealed.
4) Sealed vials were charged on stability at 2-8° C. for about 6M and 25° C./60% RH for about 2M. Table 1 show that stability data generated.

TABLE 1

| Parameter | Initial | 25° C./60% RH - 2M | 2-8° C. - 6M |
|---|---|---|---|
| Moisture content (%) | 4.05 | 3.74 | 4.0 |
| Impurity B (%) | 0.05 | 0.39 | 0.32 |
| Impurity D (%) | — | 0.94 | 0.37 |
| Specified impurity at 0.21 RRT (%) | ND | 0.54 | 0.02 |
| Specified impurity at 0.55 RRT (%) | 0.02 | 1.61 | 0.42 |
| Specified impurity at 0.75 RRT (%) | ND | 1.08 | 0.25 |
| Total impurities (%) | 0.09 | 6.45 | 1.67 |

Example 1: Pharmaceutical Formulation of Cyclophosphamide with Reduced Water Content by Vacuum Drying

| Ingredients | Quantity |
|---|---|
| Cyclophosphamide monohydrate* | 500 mg |
| Anhydrous ethanol | Qs to 1 mL |

*Water content of the input cyclophosphamide monohydrate is 6.25% w/w.

Manufacturing process:
1. The water content of cyclophosphamide monohydrate was reduced by using vacuum drying. Cyclophosphamide monohydrate was filled in 50 ml glass vial and half stoppered then the weight of the vial was taken and loaded into lyophilizer and subjected for drying under vacuum condition in lyophilizer to reduce the water content of monohydrate. Vials were checked for the final weight. Water content in the vials was around approximately 1%.
2. Anhydrous ethanol was taken and purged with nitrogen gas so that dissolved oxygen is: 1 ppm.
3. 70% of nitrogen purged anhydrous ethanol was taken.

4. Cyclophosphamide monohydrate with reduced water content from step 1) was added to ethanol of step-3 and dissolved by stirring at 1000 rpm for about 15 minutes or until clear solution forms under continuous nitrogen purging.
5. The volume was made up to 100% using nitrogen purged anhydrous ethanol and stirred for about 10 minutes for uniform distribution.
6. The bulk solution was filled in 2 ml glass vial and blanketed with nitrogen in head space and stoppered with 13 mm stopper and sealed with 13 mm seal.

Stability Data:
The sealed vials were exposed to 40° C., 25° C. and tested for description (physical stability) and total impurities (chemical stability) at 25° C. for 1 week, 2 week, 1 month, 3 months and at 40° C. for 1 week, 2 weeks. Table 2 shows the results.

TABLE 2

| Stability condition | Time period | Description | Total impurities (%) |
|---|---|---|---|
|  | Initial | Clear solution | 0.06 |
| 25° C. | 1 week | Clear solution | 0.20 |
|  | 2 week | Clear solution | 0.54 |
|  | 1 month | Clear solution | 0.97 |
|  | 3 months | Clear solution | 2.8 |
| 40° C. | 1 week | Clear solution | 0.84 |
|  | 2 week | Clear solution | 3.82 |

Example 2: Pharmaceutical Formulation of Cyclophosphamide with Reduced Water Content by Vacuum Drying Composition: Same as that of Example 1
Manufacturing Process:
1) Cyclophosphamide monohydrate was filled in glass vial, half stoppered and subjected to vacuum drying (in lyophilizer) at 25° C. at 50 mtorr pressure for about 4 hours to reduce the moisture content of cyclophosphamide monohydrate.
2) This cyclophosphamide was added to 70% of dehydrated alcohol and dissolved by stirring at 1000 rpm until clear solution formed. Then the volume was made to 100% with the remaining dehydrated alcohol.
3) Bulk solution was filled in 2 mL glass vial, stoppered and sealed.
4) Sealed vials were charged for stability at 25° C. and 2-8° C. for about 3 M.

Table 3 shows the stability data generated.

TABLE 3

| Parameter | Initial | 25° C./60% RH - 2M | 2-8° C. - 3M |
|---|---|---|---|
| Moisture content (%) | 1.0 | NA* | NA |
| Impurity B (%) | 0.03 | 0.28 | 0.15 |
| Impurity D (%) | ND** | 0.1 | 0.02 |
| Specified impurity at 0.21 RRT (%) | ND | 0.11 | ND |
| Specified impurity at 0.55 RRT (%) | ND | 0.54 | 0.16 |
| Specified impurity at 0.75 RRT (%) | ND | 0.66 | 0.11 |
| Total impurities (%) | 0.06 | 1.96 | 0.49 |

*NA: Not available
**ND: Not detectable

Example 3: Pharmaceutical Formulation of Cyclophosphamide with Reduced Water Content by Vacuum Drying Composition and process same as that of example 1.
The sealed vials were charged for stability at 2-8° C. and 25° C./60% RH for about 3 M.

Stability Data:
The samples exposed at 2-8° C. and 25° C. were tested for chemical stability i.e. total impurities at 1W, 2W, 1M, 2M and 3M time interval as shown in the below table 4.

TABLE 4

| Stability condition | Time period | Total impurities (%) |
|---|---|---|
|  | Initial |  0.05 |
| 2-8° C. | 1 week | 0.08 |
|  | 2 weeks | 0.08 |
|  | 1 month | 0.21 |
|  | 2 months | 0.19 |
|  | 3 months | 0.49 |
| 25° C./60% RH | 1 week | 0.27 |
|  | 2 weeks | 0.51 |
|  | 1 month | 1.52 |
|  | 2 months | 1.96 |
|  | 3 months | 3.92 |

Example 4: Pharmaceutical Formulation of Cyclophosphamide Prepared by Static Process with the Ratio of Cyclophosphamide Bulk Solution to Molecular Sieves as 1:0.5

| Ingredients | Quantity |
|---|---|
| Cyclophosphamide monohydrate | 500 mg |
| Anhydrous ethanol | q.s. to 1 mL |
| Molecular Sieves | Qs* |

*Quantity Sufficient.

Manufacturing Process:
1. Anhydrous ethanol was added to cyclophosphamide monohydrate and dissolved using magnetic stirrer.
2. After complete solubilization, the volume of solution was measured and made up to desired volume using anhydrous ethanol and the bulk solution was stirred for about 5 minutes.
3. Molecular sieves are added to the bulk solution of step 2) and incubated at 2-8° C. for about 8 hours [weight ratio of cyclophosphamide bulk solution to molecular sieves is 1:0.5 i.e. 1 part of cyclophosphamide bulk solution and 0.5 parts of molecular sieves].
4. The bulk solution after 8 hours incubation was filtered through 0.2 filter and analyzed for water content, assay and total impurities at intermittent intervals of 2 hours, 4 hours, 6 hours, 8 hours. Results are captured in table 5

TABLE 5

| Time interval | Water content (%) | Assay (%) | Total impurities (%) |
|---|---|---|---|
| Initial | 3.54 | 102.3 | 0.07 |
| 2 hours | 1.60 | 103.3 | 0.03 |
| 4 hours | 0.87 | 102.9 | 0.03 |
| 6 hours | 0.44 | 103.7 | 0.05 |
| 8 hours | 0.24 | 104.3 | 0.04 |

Example 5: Pharmaceutical Formulation of Cyclophosphamide Prepared by Static Process with Weight Ratio of Cyclophosphamide Bulk Solution to Molecular Sieves in 1:1 Ratio Composition same as example 3.
Manufacturing Process:
1. Cyclophosphamide monohydrate was dissolved in anhydrous ethanol using magnetic stirrer.
2. After complete solubilization, the volume of solution was measured and made up to desired volume using anhydrous ethanol. Stirring continued for about 5 minutes.
3. Bulk solution of step 2) and molecular sieves were taken in the weight ratio of 1:1 i.e. 1 part of cyclophosphamide bulk solution and 1 part of activated molecular sieve [Molecular sieves heated at 120° C. for about 12 hours].
4. The bulk solution with molecular sieves incubated or immersed in, was stored at 2-8° C. for about 8 hours.
5. After 8 hours the solution was filtered through 0.2μ filter and filled in 2 mL glass and charged for stability at 2-8° C. and 25° C./60% RH and analyzed for water content and total impurities at a time points of 1M, 2M, 3M, 6M and the results are captured in table 6.

TABLE 6

| Time interval | Water content (%) | Total impurities (%) |
| --- | --- | --- |
| Initial | 0.57 | 0.25 |
| 2-8° C. 1 M | NA* | 0.25 |
| 2-8° C. 2 M | NA | 0.32 |
| 2-8° C. 3 M | NA | 0.41 |
| 2-8° C. 6 M | 0.64 | 1.15 |
| 25° C./60% RH 1 M | NA | 1.63 |
| 25° C./60% RH 2 M | 0.53 | 2.89 |
| 25° C./60% RH 3 M | NA | 5.33 |
| 25° C./60% RH 6 M | NA | 8.82 |

*Not Analyzed.

Example 6: Pharmaceutical Formulation of Cyclophosphamide Prepared by Static Process Composition: Same as that of Example 1
Manufacturing Process:
1) 60% dehydrated alcohol was added to cyclophosphamide monohydrate in a vessel with continuous stirring at 300-400 rpm until clear solution was obtained. Then the volume was made to 100% with the remaining dehydrated alcohol.
2) Molecular sieves (ratio of cyclophosphamide bulk solution to molecular sieve 1:0.5) were added to bulk solution.
3) After holding sample with molecular sieves for 8 hours, the bulk solution was filtered. The filtered solution was filled in glass vial, stoppered and sealed.
4) Sealed vials were charged on stability at 2-8° C. and 25° C./60% RH. Table 7 shows that stability data of the formulation in comparison with initial condition.

TABLE 7

| Parameter | Initial | 25° C./60% RH - 2M | 2-8° C. - 6M |
| --- | --- | --- | --- |
| Moisture content (%) | 0.57 | 0.565 | 0.596 |
| Impurity B (%) | 0.11 | 0.30 | 0.22 |
| Impurity D (%) | ND | 0.05 | 0.02 |

TABLE 7-continued

| Parameter | Initial | 25° C./60% RH - 2M | 2-8° C. - 6M |
| --- | --- | --- | --- |
| Specified impurity at 0.21 RRT (%) | ND | 0.25 | ND |
| Specified impurity at 0.55 RRT (%) | 0.05 | 0.74 | 0.34 |
| Specified impurity at 0.75 RRT (%) | 0.08 | 0.04 | NA |
| Total impurities (%) | 0.09 | 2.86 | 1.26 |

Example 7: Pharmaceutical Formulation of Cyclophosphamide with Vacuum Drying (Example 7A) and without Vacuum Drying (Example 7B) Prepared by Static Process Using Molecular Sieves Composition is same as that of example 4.
Manufacturing Process:
1) For example 7A, cyclophosphamide monohydrate was placed in specially designed perforated trays which were kept at lyophilizer and vacuum drying was carried out as following conditions.

| Step | Shelf temp (° C.) | Chamber pressure | Time (minutes) |
| --- | --- | --- | --- |
| Freezing | | | |
| Rate | 22 | — | 15 |
| Hold | 22 | — | 15 |
| Phase-Primary drying | | | |
| Rate | 22 | 50 | 120 |
| Hold | 22 | 50 | 960 |
| | | Total time | 18 hrs. 30 minutes |

2) Cyclophosphamide monohydrate with reduced water content of step 1) (Example 5A) and without vacuum drying (Example 7B) was dissolved in half the quantity of anhydrous ethanol with stirring.
3) After complete solubilization remaining quantity of anhydrous ethanol was added and made up the volume.
4) The bulk solution of step 3 was tested for water content and was filled into vials. Half of the vials were incubated with activated (molecular sieves heated at 120° C. for 12 hours) molecular sieve and remaining half were incubated with non-activated molecular sieves.
5) The bulk solution of step 4) is filtered through 0.2μ filter and filled into glass vials.
6) All the vials were charged for stability at 2-8° C. & 25° C. for about 2 & 5 hours respectively and tested for water content. The water content data is being tabulated in table 8.

TABLE 8

| Time | Example 7A | | | | Example 7B | | | |
|---|---|---|---|---|---|---|---|---|
| | Activated | | Non-activated | | Activated | | Non-activated | |
| | 25° C. | 2-8° C. | 25° C. | 2-8° C. | 25° C. | 2-8° C. | 25° C. | 2-8° C. |
| Initial | 1.82 | | | | 3.53 | | | |
| 2 hour | 0.43 | 0.54 | 0.35 | 0.22 | 1.10 | 0.84 | 0.87 | 0.82 |
| 5 hour | 0.20 | 0.28 | 0.11 | 0.21 | 0.74 | 0.62 | 0.52 | 0.40 |

From the above data, it has been observed that the water content was significantly reduced from initial. Further the water content of the example 5A prepared by using cyclophosphamide monohydrate with reduced water content by vacuum drying along with molecular sieves in static process showed more reduction in water content.

Example 8: Pharmaceutical Formulation of Cyclophosphamide Prepared by Dynamic Process Using Molecular Sieves Composition is same as that of example 4.
Manufacturing Process:
1) Cyclophosphamide was dissolved in 90% of anhydrous ethanol with magnetic stirrer and volume was made up using remaining 10% anhydrous ethanol.
2) Molecular sieves were added in SS (stainless steel) column and the anhydrous alcohol was passed through the column at flow rate of 10 mL/minute flow rate using peristaltic pump.
3) The column was drained using peristaltic pump in reverse direction and the nitrogen gas was drained through the column.
4) The bulk solution of step 1) was passed through the column and the samples were analyzed for water content after 15 minutes, 60 minutes, 120 minutes and 180 minutes. The water content data is shown in below table 9.

TABLE 9

| Time period | Water content (%) |
|---|---|
| Initial | 3.8128 |
| 15 minutes | 1.2871 |
| 60 minutes | 0.3505 |
| 120 minutes | 0.1674 |
| 180 minutes | 0.1190 |
| Final Bulk solution | 0.2241 |

Example 9: Pharmaceutical Formulation of Cyclophosphamide Prepared by Using Dynamic Process in Recirculation Method Composition is same as that of example 4
Manufacturing Process:
1. Cyclophosphamide monohydrate was taken in a vessel.
2. Anhydrous ethanol was added to step-1 and cyclophosphamide was dissolved by using magnetic stirrer.
3. After complete solubilization, the volume of solution was made up by using anhydrous ethanol (2% excess anhydrous ethanol was added in to compensate volume loss due to water removal).
4. Cyclophosphamide bulk solution and molecular sieves are taken in 2:1 ratio. The molecular sieves type 3A was filled in SS column (20 mm ID; 250 mm length).
5. The column is rinsed with anhydrous ethanol at 10 mL/min flow rate using peristaltic pump.
6. The column is being drained by pumping liquid out of the column at 10 mL/min.
7. Cyclophosphamide bulk solution of step 3) was pumped through column of step 6) with flow rate 10 mL/min and the effluent was recirculated to the feed container containing bulk solution of cyclophosphamide.
8. The sampling is done of the bulk solution at different time intervals for water content for a total of 150 minutes.
9. The water content of the formulation collected at different time points have been analyzed and results are shown in table 10.

TABLE 10

| Time interval | Water content (%) |
|---|---|
| Initial (Untreated) | 3.5017 |
| 10 min (effluent) | 1.5674 |
| 10 min (Treated Bulk*) | 2.2465 |
| 30 min (Treated Bulk) | 1.2345 |
| 50 min (Treated Bulk) | 0.8016 |
| 70 min (Treated Bulk) | 0.5913 |
| 90 min (Treated Bulk) | 0.4306 |
| 110 min (Treated Bulk) | 0.3258 |
| 130 min (Treated Bulk) | 0.2512 |
| 150 min (Treated Bulk) | 0.2326 |
| Final Treated Bulk** | 0.3492 |

*Treated bulk means bulk solution after 10 minutes of recirculation.
**Final treated bulk is after draining out all the solution from column & tubing's

Example 10: Pharmaceutical Formulation of Cyclophosphamide by Reducing MC Using Molecular Sieves (MS) Using Dynamic Process Composition: Same as that of Example 4.
Manufacturing Process:
1) Molecular sieves [MS] column was prepared transferring molecular sieves to dried stainless steel [SS] column.
2) 60% of dehydrated alcohol was added to cyclophosphamide monohydrate in a vessel with continuous stirring at 300-400 rpm until clear solution was obtained. The volume was made up to 100% using remaining dehydrated alcohol and stirred for about NLT 10 minutes to ensure complete mixing of the solution.
3) The bulk solution was circulated through SS column in a recirculation method until moisture content is below 0.5% w/w.
4) Bulk solution was filtered through 0.22μ filter, filled, stoppered and sealed. Sealed vials are subjected to stability at 2-8° C. and 25° C./60% RH. Table 11 shows the stability data.

TABLE 11

| Parameter | Initial | 25° C./60% RH - 2M | 2-8° C. - 6M |
|---|---|---|---|
| Moisture content (%) | 0.2 | 0.2 | 0.2 |
| Impurity B (%) | 0.03 | 0.3 | 0.2 |
| Impurity D (%) | ND | ND | ND |
| Specified impurity at 0.21 RRT (%) | ND | 0.2 | 0.03 |
| Specified impurity at 0.55 RRT (%) | ND | 0.1 | 0.07 |
| Specified impurity at 0.75 RRT (%) | NA | NA | NA |
| Total impurities (%) | 0.03 | 2.5 | 1.0 |

Example 11: Pharmaceutical Formulation of Cyclophosphamide Prepared by Using Series of Columns Composition is same as that of example 4.

Manufacturing Process:

1) Anhydrous ethanol was added to cyclophosphamide taken in a vessel.
2) The mixture was dissolved using magnetic stirrer. After complete solubilization, the volume of solution was made up using anhydrous ethanol.
3) The molecular sieves are filled in two SS columns wherein both the columns are connected in series.
4) A portion of anhydrous ethanol was added to fill both the columns followed by pumping a small portion of anhydrous ethanol through the column at 6 mL/minute using peristaltic pump.
5) The column is being drained by pumping liquid out of the column at 6 mL/minute.
6) The cyclophosphamide solution of the step 2) was pumped through the column with flow rate 6 mL/minute and water content is tested for each sample collected at different time points as shown below table 12

TABLE 12

| Time period | Water content (%) |
|---|---|
| Initial | 3.5252 |
| 20 minutes | 0.3044 |
| 35 minutes | 0.4287 |
| 50 minutes | 0.4426 |
| 65 minutes | 0.4261 |
| 80 minutes | 0.4322 |

Example 12-13: Pharmaceutical Liquid Formulation of Cyclophosphamide

| Ingredients | Example-13 Quantity/mL | Example-14 Quantity/mL |
|---|---|---|
| Cyclophosphamide | 500 mg | 500 mg |
| Glycerol | 0.2 mL | 0.2 ml |
| Sodium chloride | — | 2 mg |
| Absolute Ethanol | qs to 1 mL | qs to 1 mL |

Manufacturing Process:

1. Absolute Ethanol was purged with nitrogen gas. (DO≤1 ppm).
2. Glycerol was purge with nitrogen gas. (DO≤1 ppm). Sodium chloride (Example 10) was added to glycerol and stirred until it is completely dissolved.
3. 70% of nitrogen purged Absolute Ethanol was taken.
4. Cyclophosphamide was added to step-3 and dissolved by stirring at 1000 rpm for 15 minutes i.e. until clear solution forms under continuous nitrogen purging.
5. Step-4 was added to step-2 and mixed well for uniform distribution.
6. The volume was made to 100% using nitrogen purged Absolute Ethanol and stir for 10 min for uniform distribution.
7. The bulk solution was filled in 2 ml glass vial and blanketed with nitrogen in head space and stoppered with 13 mm stopper and seal with 13 mm seal.

| Ingredients | Example 14 | Example 15 | Example 16 | Example 17 |
|---|---|---|---|---|
| | Quantity/mL | | | |
| Cyclophosphamide | 500 mg | 500 mg | 500 mg | 500 mg |
| Polyethylene glycol (PEG300) | 0.1 mL to 0.9 mL | — | — | — |
| Propylene glycol | — | 0.1 mL to 0.9 mL | — | — |
| Polysorbate 80 | — | — | 0.1 mL to 0.9 mL | — |
| Cremophor EL | — | — | — | 0.1 mL to 0.9 mL |
| Anhydrous Ethanol | Qs to 1 mL | Qs to 1 mL | Qs to 1 mL | Qs to 1 mL |

Manufacturing Process:

1. Anhydrous ethanol was purged with nitrogen gas. (DO≤1 ppm).
2. Cyclophosphamide was dissolved in 100% PEG 300 (example 11) or propylene glycol (example 12), polysorbate 80 (example 13) or cremophor EL (Example 14) and dissolved by stirring at 1000 rpm for 15 minutes i.e. until clear solution forms under continuous nitrogen purging.
3. Volume make up done with pre-purged anhydrous ethanol to 100%.
4. Bulk solution was purged with nitrogen to remove the dissolve oxygen content to minimum (preferably DO≤1 ppm).
5. The bulk solution was filled in 2 ml glass vial and blanketed with nitrogen in head space and stoppered with 13 mm stopper and seal with 13 mm seal.

The invention claimed is:

1. A stable liquid pharmaceutical formulation of cyclophosphamide comprising:
   cyclophosphamide; and
   at least one pharmaceutically acceptable excipient,
   the liquid pharmaceutical formulation having moisture content of less than about 2.0% by weight,
   wherein the liquid pharmaceutical formulation is stable when the moisture content is reduced to less than about 2.0% by weight;
   wherein total impurities are less than about 6.0% by weight when the liquid pharmaceutical formulation is stored at 2-8° C. for at least six months; and
   wherein said excipient excludes polyol organic solvent and citric acid.

2. The stable liquid formulation of claim 1, wherein the moisture content is less than about 1.0% by weight.

3. The stable liquid formulation of claim 1, wherein the concentration of cyclophosphamide is at least 0.1 g per mL.

4. The stable liquid formulation of claim 1, wherein the concentration of the cyclophosphamide is 0.5 g per mL.

5. The stable liquid formulation of claim 1, wherein said liquid formulation has less than about 1.5% of impurity D, represented by the structure IV

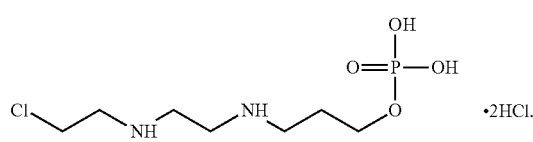

(IV)

6. The stable liquid formulation of claim 1, wherein said liquid formulation has less than about 1.5% of impurity B, represented by the structure III

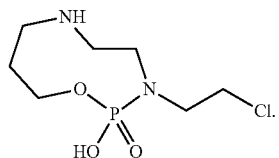

(III)

7. The stable liquid formulation of claim 1 wherein the cyclophosphamide in the formulation is cyclophosphamide monohydrate.

8. The stable liquid formulation of claim 1 wherein the pharmaceutically acceptable excipient is selected from the group comprising of ethanol, polysorbates, cyclodextrins, dimethyl acetamide, polyethoxylate castor oil or combination thereof.

9. The stable liquid formulation of claim 1 wherein total impurities are less than about 6.0% by weight when the liquid pharmaceutical formulation is stored at 2-8° C. for six months.

* * * * *